United States Patent
Richelsoph et al.

(10) Patent No.: US 7,972,366 B2
(45) Date of Patent: *Jul. 5, 2011

(54) BONE PLATE AND SCREW RETAINING MECHANISM

(75) Inventors: Marc Richelsoph, Bartlett, TN (US); Jay Adams, Bartlett, TN (US)

(73) Assignee: Aesculap Implant Systems, LLC, Center Valley, PA (US)

( * ) Notice: Subject to any disclaimer, the term of this patent is extended or adjusted under 35 U.S.C. 154(b) by 1227 days.

This patent is subject to a terminal disclaimer.

(21) Appl. No.: 10/401,997

(22) Filed: Mar. 28, 2003

(65) Prior Publication Data

US 2003/0187440 A1  Oct. 2, 2003

Related U.S. Application Data

(62) Division of application No. 10/095,720, filed on Mar. 12, 2002, now Pat. No. 6,695,846.

(51) Int. Cl.
*A61B 17/80* (2006.01)
(52) U.S. Cl. ...................................... 606/290
(58) Field of Classification Search .............. 606/61, 606/69–73; 608/61
See application file for complete search history.

(56) References Cited

U.S. PATENT DOCUMENTS

| 5,520,690 | A  | * | 5/1996  | Errico et al. ............ 606/287 |
| 5,607,426 | A  | * | 3/1997  | Ralph et al. ............ 606/287 |
| 5,735,853 | A  |   | 4/1998  | Olerud |
| 5,876,402 | A  | * | 3/1999  | Errico et al. ............ 606/287 |
| 6,022,350 | A  | * | 2/2000  | Ganem ................. 606/272 |
| 6,139,550 | A  |   | 10/2000 | Michelson |
| 6,599,290 | B2 | * | 7/2003  | Bailey et al. ............ 606/86 B |
| 6,602,255 | B1 |   | 8/2003  | Campbell et al. |
| 2001/0047172 | A1 |   | 11/2001 | Foley et al. |
| 2002/0183747 | A1 |   | 12/2002 | Jao et al. |

FOREIGN PATENT DOCUMENTS

| EP | 1 169 981 A2 | 1/2002 |
| WO | WO 99/56653 | 11/1999 |
| WO | WO 00/18312 | 4/2000 |
| WO | WO 01/26567 A1 | 4/2001 |

* cited by examiner

*Primary Examiner* — Anu Ramana
(74) *Attorney, Agent, or Firm* — RatnerPrestia

(57) ABSTRACT

A bone plate assembly utilizing at least one bone screw for fixation of adjacent bones of a spine including a base plate having at least one aperture extending therethrough and screw retaining mechanism mounted and movable on the plate between locked and unlocked positions relative to the aperture for preventing the bone screw from backing out from the base plate. Furthermore, a device for placement into an aperture of a base plate including a screw retaining mechanism mountable and movable on a plate between locked and unlocked positions relative to an aperture for preventing a bone screw from backing out from the base plate.

15 Claims, 6 Drawing Sheets

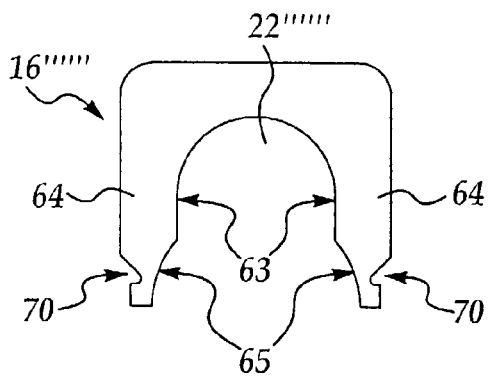
Figure 16A
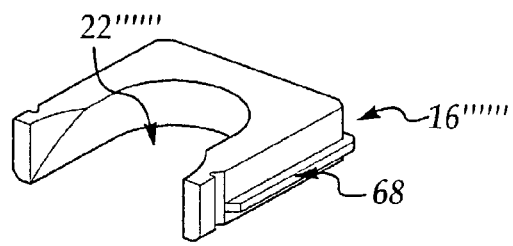
Figure 16B
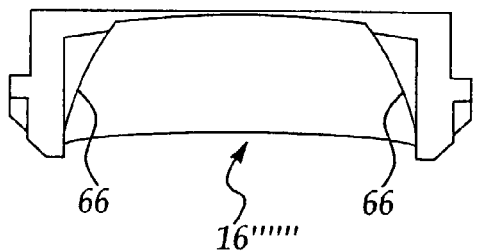
Figure 16C
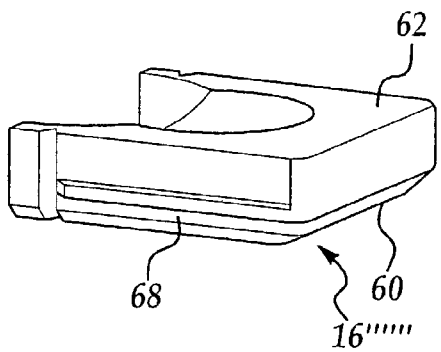
Figure 16D
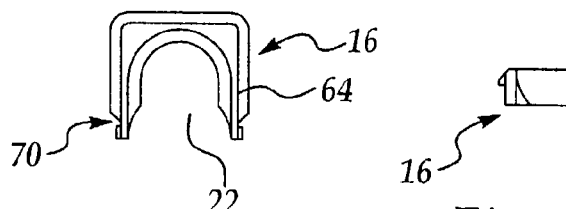
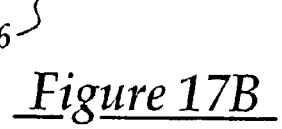
Figure 17A
Figure 17B
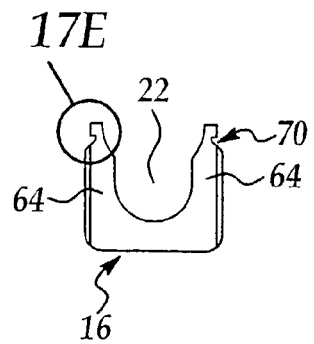
Figure 17C
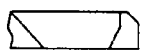
Figure 17D
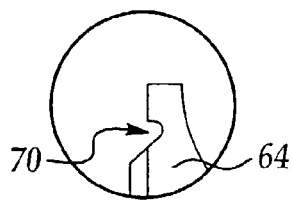
Figure 17E

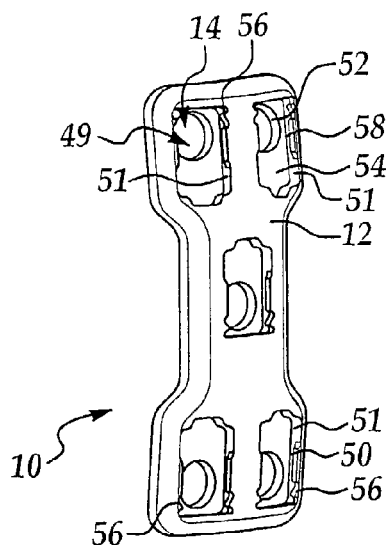
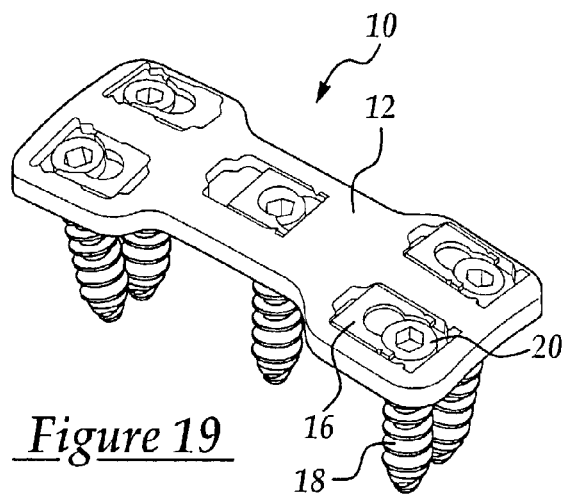
Figure 18
Figure 19
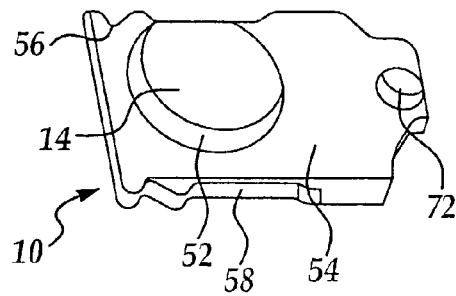
Figure 20
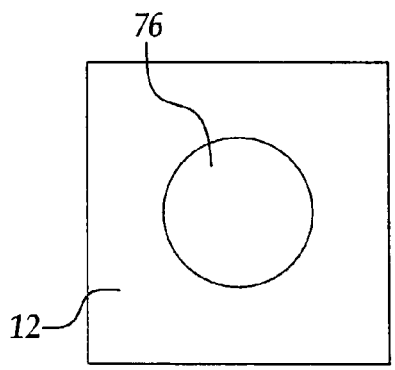 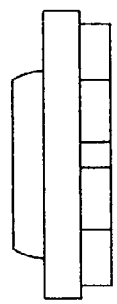 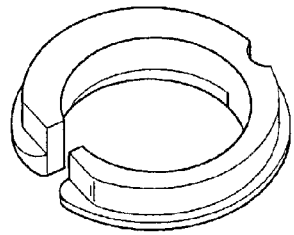
Figure 21A   Figure 21B   Figure 21C

BONE PLATE AND SCREW RETAINING MECHANISM

CROSS RELATED REFERENCE SECTION

This application is a divisional application of U.S. patent application Ser. No. 10/095,720, filed Mar. 12, 2002, now U.S. Pat. No. 6,695,846, which is incorporated herein by reference.

BACKGROUND OF THE INVENTION

1. Field of the Invention

The present invention relates to bone fixation plate assemblies. More specifically, the present invention relates to a mechanism for preventing the displacement of a screw.

2. Description of Related Art

Spinal fixation has become a common approach in treating spinal disorders, fractures, and for fusion of vertebrate. A common devise used for spinal fixation is a bone fixation plate assembly. Typical bone fixation plate assemblies have a relatively flat, rectangular plate with a plurality of apertures therethrough. Fasteners, such as bone screws, are utilized to secure the bone fixation plate assembly. The screws are firmly tightened to secure the bone fixation plate to the bone or bones to be fixed. There are numerous examples of bone fixation plates existing in the art. These are illustrated in U.S. Pat. No. 5,364,399 to Lowery et al., U.S. Pat. No. 5,601,553 to Trebing et al., U.S. Pat. No. 6,017,345 to Richelsoph, U.S. Pat. No. 6,152,927 to Farris et al., U.S. Pat. No. 6,235,034 B1 to Bray, U.S. Pat. No. 6,139,550 to Michelson, and U.S. Pat. No. 6,258,089 B1 to Campbell et al. The above referenced patents are cited as examples illustrating the general state of the art with regard to bone fixation plate technology. Generally, these types of devices can be utilized for the fixation of any bone or bones, but are more particularly suited for the fixation of the spine with regard to the cervical, lumbar and/or thoracic regions.

The basis of interior fixation or plating is to approach the spine from the anterior or interior-lateral side and use the screws to solidly mount the bone fixation plate to the affected vertebrate. This approach is commonly used in cases of trauma, tumors, and degenerative conditions. Often, in addition to the application of a bone fixation plate, graft material can be combined in an attempt to permanently fuse together adjacent vertebrate. The graft material can consist of bone grafts obtained from other bones in the patient's body or from cadaver bones.

A common problem associated with the use of such bone fixation plates is a tendency of the bone screws to "back out" or pull away from the bone onto which they were fixed. This problem occurs primarily due to the normal motion of the body and the spine. Since the spine is a very dynamic entity and is constantly moving, this problem is especially prevalent in areas of high stress such as the spine. Once the screw becomes loose and pulls away from the bone, the head of the screw can rise above the surface of the bone fixation plate and even work its way completely out of the bone. This creates a number of potentially serious problems given the number and proximity of blood vessels and other critical structures near the locations of spinal fixation plate assemblies.

A number of various designs have been brought forth in attempts to prevent screws from pulling away from the bone and/or to prevent the screws from backing out or pulling away from the surface of the bone fixation plate. For example, the Lowery et al. patent discloses an anterior cervical plating system incorporating a locking screw, which engages the heads of the bone screws used to secure the cervical plate to the vertebrae. The locking screw is positioned above the bone screws and is driven against the heads of the bone screws to rigidly fix the bone screws to the plate. For this locking mechanism to work however, the distance between the heads of the bone screws must be kept to a minimum, thereby limiting the potential applications of the bone fixation plate. Additionally, while the Lowery et al. patent allows for the bone screws to be angled, if the screws are not angled exactly the same amount, which is very difficult to achieve, the locking screw cannot adequately contact both bone screw heads.

Another example of a mechanism for preventing bone fixation screws from backing out or becoming dislodged from the bone is set forth in the Trebing et al. patent discussed above. The Trebing et al. patent discloses a mechanism whereby the bone fixation plate is threaded and is used in combination with a bone screw having both bone engaging threads and a threaded portion near the head of the bone screw which is complimentary to the threaded hole in the bone fixation plate. In this mechanism, the screw is rigidly fixed to the bone fixation plate. It is possible however, to lock the bone screw to the bone fixation plate while leaving a gap between the bone fixation plate and the bone. This problem can cause inferior fixation of the bone or even total failure of the fixation.

Various other mechanisms used to prevent bone screws from pulling out of bones include cams, which engage and lock the screws and the use of expanding head screws, which expand outwardly when adequate force is applied thereto to engage the holes in the bone fixation plate. All of these particular designs have drawbacks including potential for breakage or requiring particular precision and alignment in their application in order to correctly work.

Another apparatus for preventing bone screw back-out from a bone fixation plate is shown in U.S. Pat. No. 5,578,034, issued Nov. 26, 1996, to Estes. The Estes patent discloses a system for internal fixation of bone that includes a bone fixation plate having a number of bores therethrough, a corresponding number of screws each having an enlarged head portion, and an elongated shaft portion defining bone engaging threads thereabout and a non-threaded portion between the head and the threaded portions, and a corresponding number of screw anti-backout members each having a bore therethrough. The screw anti-backout members are inserts positioned within the bores of the fixation plate and are initially sized to slidingly receive an elongated screw shaft therethrough. During application of the fixation plate, the bone screws are advanced through the bone fixation plate bores and the screw anti-backout members which are positioned within the plate bores to screw the bone fixation plate to the underlying bone. Thereafter, the apparatus is sufficiently heated to shrink the bores of the screw anti-backout members, thereby trapping the non-threaded portion of the screw shafts located between the fixation plate and the threaded portions. The anti-backout collars are immobilized within the bore of the fixation plate. The collar and fixation plate remain in fixed relationship to each other after fixation to the underlying bone.

Other types of inserts or collars have been used with bone fixation plates for a variety of reasons such as those shown in U.S. Pat. No. 4,388,921, issued Jun. 21, 1983, to Sutter et al. and U.S. Pat. No. 5,607,428, issued Mar. 4, 1997, to Lin. Sutter et al. discloses a bone fixation plate in which sleeves are placed in openings provided in a bone fixation plate. A screw is placed through the sleeve and into the underlying bone. By tightening the screw, the sleeve is clamped in place with relation to the bone fixation plate thus assuring that the fixation plate will stay rigidly connected with the screws.

The Lin patent discloses a bone fixation plate having a direction adjusting ring disposed in at least one hole in the fixation plate. Upon insertion and tightening of the threaded bone screw, arresting edges of the direction adjusting ring are urged into engagement within the hole to securely fix and retain the direction adjusting ring therein.

Other examples of recent systems that have been built utilize small setscrews or locking screws. Others utilize bulky covers or cams to engage screws to achieve a mechanism for locking and retaining the screw to the plate. One such example is illustrated in U.S. Pat. No. 6,152,927 to Farris et al. The Farris et al. patent discloses a set screw that is longer so that it can remain in the plate and in the bone even if it is backed out a certain distance. The screw can be backed out further so that the bone screws have clearance to enter the holes in the plate. (See FIG. 19). The end result is the screw penetrates through the plate and creates an unnecessary load against the vertebrate, which opposes the bone screws and tends to try and lift the plate off the bone.

U.S. Pat. No. 6,258,089 to Campbell et al. discloses another type of mechanism that prevents the screw from backing out. The Campbell et al. patent discloses the use of a tab that is integral to the plate and machined into the plate therein. The tab must be bent to cover the screw to prevent it from backing out. If a surgeon needs to revise or to fix the screw position, the tab needs to be bent back prior to accessing the screw. As a result, stress is created in the metal and mostly will possibly require the replacement of the plate.

Another example is found in U.S. Pat. No. 6,139,550 to Michelson. The Michelson patent discloses the use of an apparatus thereof for locking three set screws at once utilizing a cam mechanism. In order to guarantee the cam lobes stop exactly where they must be to engage the three screws, the threads in the plate and the threads on the cam must be carefully controlled and timed so that the threads begin exactly the same.

Finally, another example of bone plate and screw guide mechanism is disclosed in U.S. Pat. No. 6,235,034 B1 to Bray. The Bray patent discloses a bone plate including a base plate, wherein a retaining plate is also provided therein. The retaining plate is fixedly attachable to the base plate and the retaining plate covers at least a portion of each of the bone screws. The retaining plate is secured to the base plate with set screws that are inserted into set screw apertures located therethrough. This invention therefore requires a separate screw to retain the bone screws within the base plate and bones.

Accordingly, there is a need for a bone fixation plate assembly that allows positive, rigid fixation of a bone fixation plate to a bone, while allowing movement, stress, or dynamic load sharing of the adjacent vertebrate. More specifically, there is a need for a bone fixation plate assembly that provides a simple reversible locking mechanism built into the plate that prevents the screw from backing out. Additionally, there is a need for a mechanism that maintains and/or prevents the screw from backing out from a bone plate.

SUMMARY OF THE INVENTION

According to the present invention, there is provided a bone plate assembly utilizing at least one bone screw for fixation of adjacent bones of a spine including a base plate having at least one aperture extending therethrough and a screw retaining mechanism mounted and movable on the plate between locked and unlocked positions relative to the aperture for preventing the bone screw from backing out from the base plate. The present invention also provides for a device for placement into an aperture of a base plate including a screw retaining mechanism mountable and movable on a plate between locked and unlocked positions relative to an aperture for preventing a bone screw from backing out from the base plate. Additionally, the present invention provides for a snap ring for placement into an aperture of a base plate including a screw retaining mechanism mountable and movable on the plate between locked and unlocked positions relative to the aperture for preventing a screw from backing out from the base plate. Also, the present invention provides for a device for placement into an aperture of a base plate, wherein the aperture includes a pocket, the device including a screw retaining mechanism mountable and movable on the plate between locked and unlocked positions relative to the aperture for preventing a screw from backing out from the base plate. Finally, the present invention provides for a bone plate assembly utilizing at least one bone screw for fixation of adjacent vertebrae of a spine including a base plate having at least one aperture extending therethrough, wherein at least one aperture is an elongated slot having a hole extending therethrough and walls forming a spherical seat a distance along a length of the slot to allow the screw to enter through the hole and screw retaining mechanism mounted and movable on the plate between locked and unlocked positions relative to the aperture for preventing the bone screw from backing out from the base plate.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 1 is a top view of one embodiment of the screw retaining mechanism of the present invention, wherein FIG. 1A illustrates the screw retaining mechanism in a locked positioned, while

FIG. 2 has views of another embodiment of the screw retaining mechanism of the present invention, wherein FIG. 2A is a top view, while

FIG. 3A is a cross-sectional view of an embodiment of the bone plate assembly of the present invention illustrating the machining and location of a pocket within the bone plate assembly without the screw retaining mechanism, while

FIG. 6 illustrates various views of an embodiment of the bone plate assembly of the present invention, wherein

FIG. 7 illustrates various views of an embodiment of the bone plate assembly of the present invention having five apertures extending therethrough, wherein

FIG. 16 illustrates another embodiment of the screw retaining mechanism of the present invention that is substantially "U" shaped;

FIG. 17 is an engineering diagram illustrating the embodiment of the screw retaining mechanism shown in FIG. 16;

FIG. 18 is an illustration of an embodiment of a bone plate assembly of the present invention wherein the assembly utilizes the screw retaining mechanism shown in FIG. 16;

FIG. 19 is another illustration of the bone plate assembly shown in FIG. 18, wherein the center screw retaining mechanism is in a locked position, while the other screw retaining mechanisms are in unlocked positions;

FIG. 20 is a close-up view of the aperture located on the bone plate assembly shown in FIGS. 18 and 19; and FIG. 21 is an illustration of another embodiment of the bone plate assembly of the present invention, wherein FIG. 21A is a perspective view of a base plate having a hole for accommodating an insert, as shown in FIG. 21B, which in turn accommodates the screw retaining mechanism illustrated in FIG. 21C.

DETAILED DESCRIPTION OF THE INVENTION

Figure 1A:
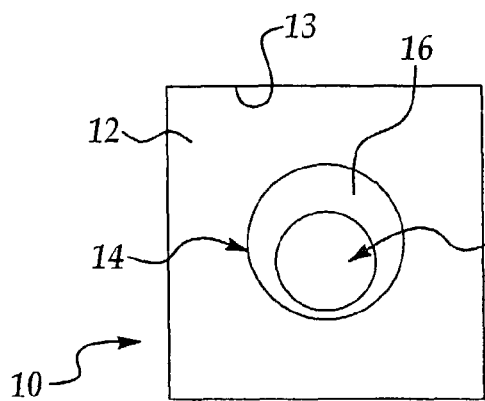

A bone plate assembly constructed in accordance with the present invention is generally indicated by 10 in the figures. Generally, the bone plate assembly 10 includes a base plate 12 having at least one aperture 14 extending therethrough and a screw retaining mechanism 16. The bone plate assembly 10 utilizes at least one bone screw 18 for the fixation of bones, and more specifically adjacent vertebrae. The key feature of the present invention is not only the bone plate assembly 10, but also the screw retaining mechanism 16. The screw retaining mechanism 16 prevents the bone screw 18 from backing out from its fixed position within the aperture 14 of the base plate 12 and within the bone. Although there are numerous embodiments of both the bone plate assembly 10 and the screw retaining mechanism 16, they all have the common characteristic of being able to cover at least a portion of the bone screw 18 after the screw 18 is inserted and turned into its fixed position within the base plate 12 and bone therein.

The present invention has numerous applications within various fields. Although most of the applications of the present invention involve the medical field, the present invention, particularly the screw retaining mechanism 16, can be utilized in any other field outside the medical setting, such as the mechanical arts, automotive arts, and other related industries. Preferably, the present invention is useful in the fixation of any bones, but in particular the vertebrae.

The bone plate assembly 10 and the screw retaining mechanism 16 of the present invention can all be constructed of any suitable material known to those of skill in the art. Preferably, the bone plate assembly 10 and the screw retaining mechanism 16 are constructed of suitable material that are compatible with uses and environments into which they are utilized. Both the bone plate assembly 10 and the screw retaining mechanism 16 are constructed of metallic materials that include, but are not limited to, titanium, stainless steel, and any other metallic alloys known to those of skill in the art. Additional materials can also be utilized either alone or in combination with the metallic materials described herein. For instance, various plastics can be used. Typically though, any of the material used to construct the present invention should be very strong, non-reactive, and non-antigenic to biological systems. If the present invention is utilized outside of biological systems however, the aforementioned characteristics are not necessarily required.

The terms "aperture" or "apertures" 14 as used herein, are meant to include, but are not limited to, any circular hole, oblong hole, slot, elongated slot, through hole, void, and any other similar opening. The aperture 14 should be large enough to accommodate at least a shaft of a screw 18 and preferably the entire screw head 20. The aperture 14 is not necessarily limited to just the size of the screw 18 and screw head 20. The aperture 14 can be larger than the screw head 20, but also have a spherical seat or other similar, machined portion on the base plate 12 located therein to prevent the screw from passing completely through the aperture 14. Additionally, the aperture 14 can be an elongated slot wherein the screw 18 is capable of sliding within the slot, but is also able to accommodate the screw retaining mechanism 16 to prevent the screw 18 from backing out from its fixed position.

Figure 7A:
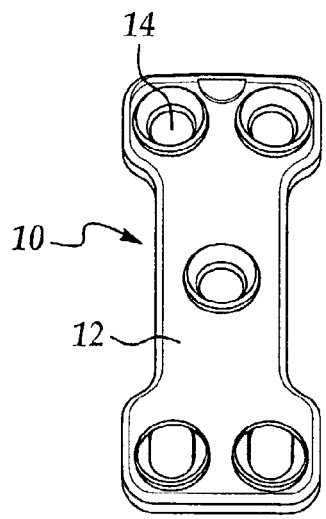
FIG. 7A is a top view.
Figure 7B:
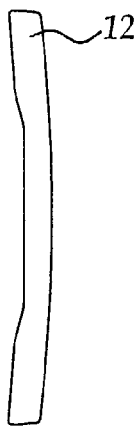
FIG. 7B is a side view demonstrating the curvature of the assembly, and 7C is a perspective view.
Figure 7C:
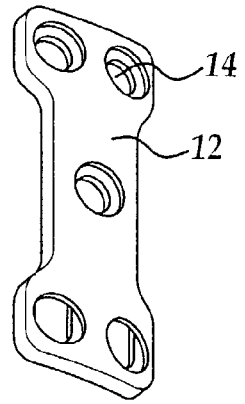

The base plate 12 varies in size and shape. The base plate 12 can be curved, as depicted in FIG. 7, to match the curvature of the spinal column. Alternatively, the base plate 12 can be completely flat. The base plate 12 can be as small as the bones of the spinal column or as large as a femur. According to the location and use, the size and shape of the base plate 12 can vary. The base plate 12 also includes at least one aperture 14 extending through an upper surface 13 of the base plate 12 and through a lower surface 15. The upper surface 13 is the location of the initial insertion of the bone screws 18 and is not touching any bone surface thereon. The lower surface 15 is closest to the spinal column and typically touches the surface of the bones to which the base plate 12 is affixed. The number of apertures 14 located on the base plate 12 vary according to design, location and severity of fixation desired. For instance, an embodiment illustrated in FIG. 7 includes five apertures 14 located thereon. This base plate 12 has three spherical seats and through hole pockets with two slotted pockets to allow translational screw motion therein. To one skilled in the art, these two variations can be combined to provide for numerous other configurations. Thus, the present invention is not limited to those embodiments described herein. Of note, the Figures illustrate a bone plate assembly 10 for cervical areas and are curved in both the longitudinal and transfer planes. Other plates of the present invention however, can utilize the screw retaining mechanism 16, while being flat or curved as is required or designed by those skilled in the art.

As previously mentioned, the apertures 14 vary in size according to the desired design of the base plate 12. For instance, the aperture 14 can be an elongated slot that allows for a substantial margin of adjustment and proper location of the screw 18 and bone plate assembly 10. As a result, the screws 18 can be made to slide freely within the slots along with the screw retaining mechanism 16. The spacing and orientation of the apertures 14 within the bone plate assembly 10 can be designed and selected so as to achieve a desired load sharing arrangement between the screws 18 disposed in the various combinations of apertures 14 described herein. That is, the bone plate assembly 10 can be tailored to a specific application such that the load carried by each screw 18 can be distributed in a desired manner, including load shifting after the bone plate assembly 10 has been affixed to the bones. The bone plate assembly 10 can accommodate the dynamic environment into which it is utilized without incurring the drawbacks of prior art devices previously described above.

The apertures 14 of the bone plate assembly 10 are specifically designed and machined into the base plate 12 therein to allow for the insertion of a screw retaining mechanism 16 over the bone screw 18 that is extended through the aperture 14 of the bone plate assembly 10. The apertures 14 are machined according to desired designs and according to the type of screw retaining mechanism 16 that is utilized. Therefore, if a circular or disc shaped screw retaining mechanism 16 is utilized, then the appropriate aperture 14 is machined into the bone plate assembly 10 in order to accommodate that particular type of screw retaining mechanism 10. Alternatively, the aperture 14 can be designed for use with a specially designed insert for accommodating the screw retaining mechanism 16. Such an insert for the screw retaining mechanism 16 is described below.

The screw retaining mechanism 16 can be any structure capable of preventing the screw 18 from backing out from its fixed positioned. Basically, the screw retaining mechanism 16 partially covers at least a portion of the screw 18, and more specifically the screw head 20, to prevent the screw 18 from backing out from its fixed position within the bone and from within the aperture 14 extending therethrough within the base plate 12 of the bone plate assembly 10. Various embodiments of the screw retaining mechanism 16 are described herein.

Figure 1B:
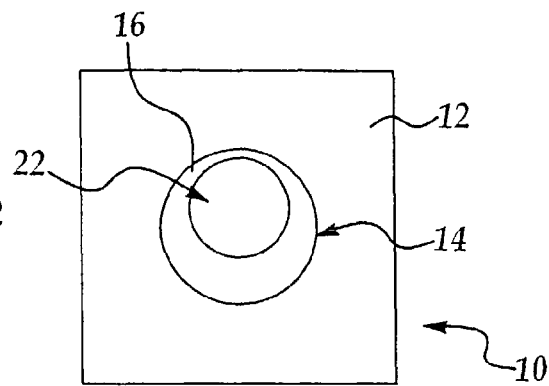
FIG. 1B illustrates the screw retaining mechanism in an unlocked position.

In one embodiment of the present invention, the screw retaining mechanism 16 is a metal disc that is capable of rotating within the aperture 14. The disc includes a smaller circumference hole 22 that is drilled through the disc such that the hole is off center relative to the larger outer diameter of the aperture 14 located on the bone plate assembly. (See, FIGS. 1A and 1B). If the disc is rotated about the center of the outer diameter of the aperture 14, then the small hole 22 changes its location because the smaller hole 22 is not on the same center as the outer diameter of the aperture 14 (See FIG. 1B). As a result, the disc changes from a locked position (FIG. 1B) to an unlocked position (FIG. 1A) by simply rotating the disc about the center of the outer diameter of the aperture 14. In its locked position, the disc or screw retaining mechanism 16 partially covers at least a portion of the screw head 20 to prevent the screw head 20 from backing out. While in the unlocked position, the screw retaining mechanism 16 allows for easy access to the screw head 20 to remove it from the base plate 12 and fixed bone location therein. The hole 22 located within the screw retaining mechanism 16 changes from an aligned position with the screw head 20 to a non-aligned position that partially covers at least a portion of the screw head 20 therein.

Figure 2A:
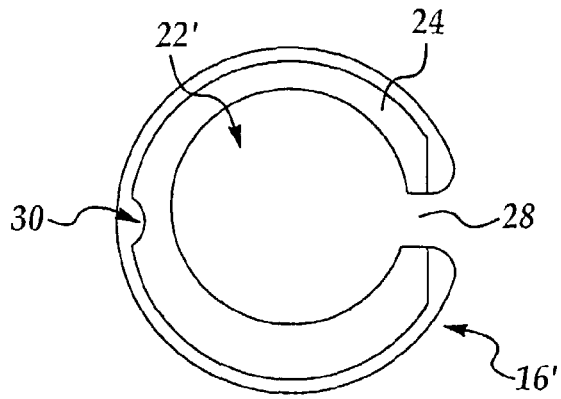
Figure 2B:
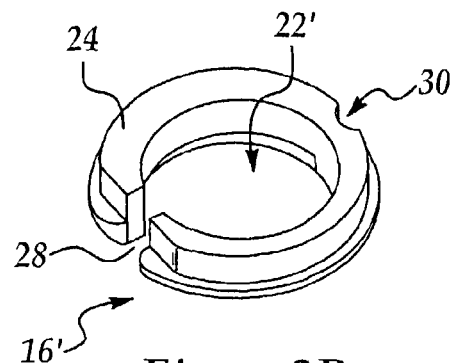
FIG. 2B is a perspective view.

In another embodiment of the present invention, the screw retaining mechanism 16' is a snap ring as shown in FIGS. 2A and 2B. This ring includes an outer cylindrical portion 24 with a flange 26 radially extending outward. A hole or aperture 22' is drilled through the screw retaining mechanism 16 with the location of the center point of that hole or aperture 22' eccentric to the center point of the outer cylindrical portion 24. The ring is then split to form a gap 28 and thus creates a screw retaining mechanism 16' that is substantially "C" shaped. As a result, placement of the ring into the machined aperture 14 of the base plate 12 occurs by simply squeezing the ring so that the gap 28 is reduced. The ring then is mounted into the aperture 14 and the pressure is released from the ring to allow the ring to spring open. The ring is now affixed and mounted within the aperture 14. The ring can also include a notch or groove 30 that is located 180° from the gap 28 formed from the split on the ring. This notch or groove 30 matches and operatively engages an extension 41 on the base plate 12 to hold the screw retaining mechanism 16' in place after it is turned to its locked position and preventing the screw head 20 from backing out.

Figure 3A:
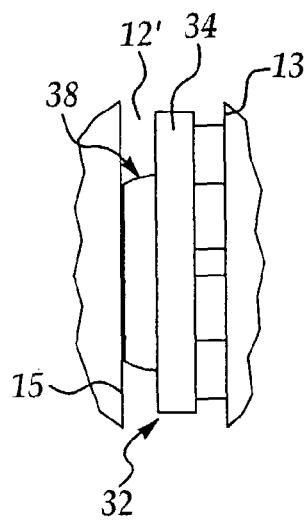
Figure 3B:
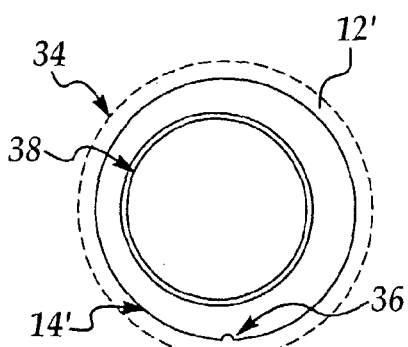
FIG. 3B is a top view of the same embodiment of the bone plate assembly.

The screw retaining mechanism 16' described above and illustrated in FIGS. 2A, 2B and 4 is used with the base plate 12' having a pocket 32 machined into the aperture 14 located therein (See, FIG. 4). The pocket 32 serves as a place for mounting and securing the screw retaining mechanism 16' thereon. The pocket 32 allows for the rotation of the screw retaining mechanism 16' about its own axis. The pocket 32 machined therein is basically a blind hole that is slightly larger the cylindrical portion of the screw retaining mechanism 16'. The pocket 32 further includes a cylindrical undercut 34 and locking tab 36 as described above. A spherical portion 38 and opening 40 is machined into the plate that can accept the screw 18. This spherical portion 38 and opening 40 is located such that the hole or aperture 22' located within the screw retaining mechanism 16' lines up with the opening 40 located within the spherical portion 38 during screw insertion. The opening 40 of the spherical portion 38 is eccentric to the aperture 14' located on the base plate 12'. This embodiment of the base plate 12' is further illustrated and shown in detail in FIGS. 3A and 3B.

Figure 4:
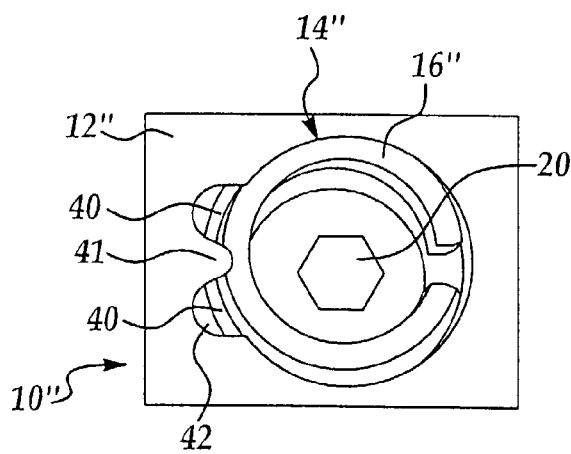
FIG. 4 illustrates an embodiment of the bone plate assembly including the base plate having an aperture and the screw retaining mechanism mounted within the aperture of the base plate, wherein a bone screw is extending therethrough and the screw retaining mechanism is in a locked position to prevent the screw from backing out from the base plate.

FIG. 4 illustrates another embodiment of the present invention. This embodiment is similar to the embodiment illustrated in FIGS. 2 and 3. FIG. 4 shows a close up of the bone plate assembly 10" wherein the screw retaining mechanism 16" is mounted within the aperture 14" of the base plate 12" with the bone screw 18 extending therethrough. FIG. 4 illustrates the screw retaining mechanism 16" in its locked position. As shown therein, a portion of the screw retaining mechanism 16" covers at least a portion of the screw head 20, thereby preventing the screw 18 from backing out of the base plate 12" and the fixed position within the bone. In this particular embodiment however, as opposed to the embodiment depicted in FIGS. 2 and 3, there are two locking tabs 40 located on the screw retaining mechanism 16". These locking tabs 40 have corresponding grooves 42 located on the outer diameter or the aperture 14" of the base plate 12" for engaging and mating with the locking tabs 40. The grooves 42 are simply machined into the base plate 12" utilizing an end mill or other similar device known to those of skill in the art.

Figure 5:
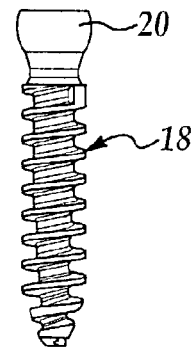
FIG. 5 is a side view of a bone screw with a spherical head that can be typically utilized with the present invention.

Although FIG. 4 illustrates the screw retaining mechanism 16" as being a relatively fixed and immobilizing device, the screw retaining mechanism can be altered or varied to allow for variation in the extent of locking. For example, one variation is to allow the screw retaining mechanism 16" to rotate over the top of the screw head 20 with no contact at all with the screw head 20 thereon. Such a screw retaining mechanism 16" prevents the screw 18 from backing out of the base plate 12", while allowing the screw head 20 to pivot freely. When the screw head 20, which is spherical, is free, it is capable of rotating within the spherical seat 38 of the base plate 12" therein. Such a spherical screw 18 is illustrated in FIG. 5. Another variation includes forcing the screw retaining mechanism 16" to engage and fully contact the screw head 20 directly. Therefore, the screw retaining mechanism 16" locks and immobilizes the screw 18 in the fixed position with no movement at all. The screw retaining mechanism 16" can be adjusted for any of the screw retaining mechanisms 16" and bone plate assemblies 10 described herein. Further variations include only partially locking or immobilizing the screw 18 with the screw retaining mechanism 16". Thus, only partial motion or no motion at all is allowed by the screw retaining mechanism 16" when it is turned to various positions on the base plate 12".

Figure 6A:
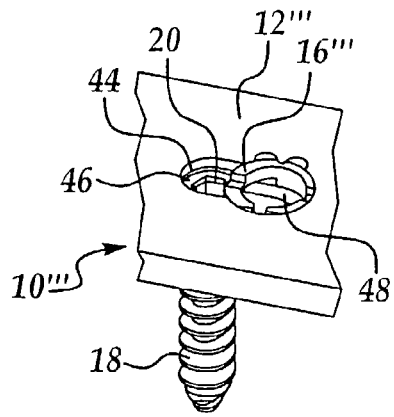
FIG. 6A is a perspective view of the bone plate assembly including a slotted aperture accommodating the screw retaining mechanism in a locked positioned.
Figure 6B:
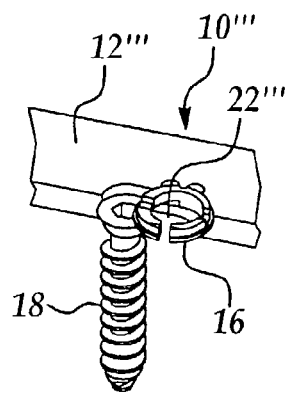
FIG. 6B is a perspective cross-sectional view of the bone plate assembly wherein the screw retaining mechanism is in a locked positioned.
Figure 6C:
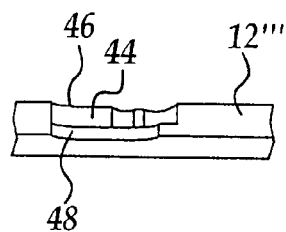
FIG. 6C is a cross-sectional view of the bone plate assembly and more specifically the aperture extending therethrough.

Another embodiment of the present invention involves altering the base plate 12''' such that the aperture 14 is now an slot 44 having walls 46 with a spherical seat 48 stretched the length of the slot 44. This design allows for different variations. For instance, the slot 44 can be machined so that the slot 44 varies in size along the length of the slot 44. The slot 44 can be large enough to accommodate a screw 18 and its screw head 20, but the spherical seat 48 does not allow for the screw 18 to be passed entirely through the base plate 12'''. Then, the slot 44 is slightly larger to accommodate at another end to accommodate the screw retaining mechanism 16''' therein. In operation, the screw 18 is inserted at one end of the slot 44 and secured therein. Then, the screw retaining mechanism 16''' is mounted into the slot 44 at the other end. Next, depending on whether the locked or unlocked position is desired, the screw retaining mechanism 16''' is turned appropriately. Alternatively, the design of the slot 44 can be changed to allow for the screw 18 to be inserted into the opening 22 of the screw retaining mechanism 16'''. In either embodiment, the screw 18 can travel the length of the spherical seat 48 and slot 44. Moreover, when the screw retaining mechanism 16''' is turned to the locked position, the screw 18 is prevented from backing out while still allowing it to travel along its longitudinal axis. These embodiments are further illustrated in more detail in FIGS. 6A, 6B, and 6C.

In any of the previously described embodiments of the present invention, prevention of the screw 18 from backing out is critical. Additionally, motion, or partial motion of the screw 18 is also desirable since it permits loading of the bone graph during the healing process. In the case of semi rigid fixation, the bone screw 18 can move somewhat relative to the plate during the healing process of the spine. It has been suggested that semi rigid fixation is preferable for the treatment of degenerative diseases of the spine. In cases where a graph implanted in place of a disease, disk or vertebral body, the presence of a screw 18 capable of some rotation ensures continual loading of the graph. This continual loading avoids stress shielding of the graph, which in turn increases the rate of fusion and incorporation of the graph into the spine.

There are at least two mechanisms of load sharing that are possible with the present invention. The screw head can pivot in the spherical seat 38 or the screw 18 can translate along the slot, as shown in U.S. Pat. No. 6,017,345. Either way provides a different method of loading the graph in the spine. Using the head 20 to pivot requires the vertebral bodies attached to the screws 18 to pivot around the screw heads 20 thus changing the angle of the vertebral bodies during the healing process. Translational loading permits the vertebrae to remain loaded by simply sliding along the long axis of the plate thereby maintaining spinal alignment. The bone plate assembly 10 of the present invention can perform both techniques or prevent them both by allowing rigid fixation of the screws to the plate. Therefore, a myriad of options and variations of the present invention are possible.

Figure 8:
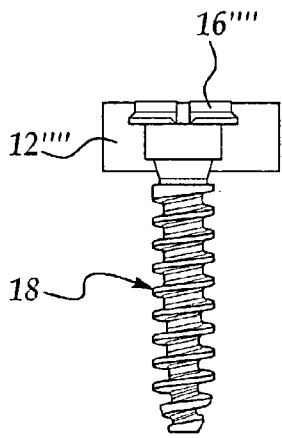
FIG. 8 is a close up, cross-sectional view of the aperture of the base plate containing a bone screw, wherein the spherical seat is replaced with a simple pocket.
Figure 9:
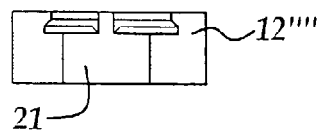
FIG. 9 is a close-up, cross-sectional view of the bone plate assembly of the present invention specifically showing the aperture of the base plate without the screw retaining mechanism and screw extending therethrough.
Figure 10:
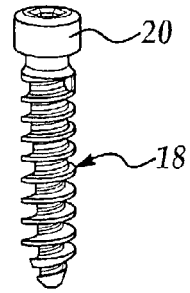
FIG. 10 is a perspective view of a screw utilized with the present invention that is particularly suited for use with the embodiments of the bone plate assembly illustrated in FIGS. 8 and 9.

Another variation of the present invention is an embodiment wherein no rotation of the screw head is required during a surgical procedure or during the healing process. This may be the case where a fracture occurs and the plate serves merely to hold the fragments in alignment and motion is possibly detrimental to the healing process. In these particular cases, the spherical seat 38 in the plate 12"" is replaced by a simple lined hole 21 and the screw head 20 is altered to be cylindrical in nature also. In addition, this same concept can be supplied to the translational aspect. In certain cases for cervical or trauma plating, it may be desirable to have one or more screws 18 on the plate 12"" be able to translate without being able to rotate about the spherical head 20. Therefore, if the spherical wall slot is replaced by rectangular wall, the head 20 can be prevented from rotating in multiple planes while still being prevented from backing out by the screw retaining mechanism 16"". The embodiment with the spherical seat 38 replaced with a simple pocket 21 is further illustrated in FIGS. 8 and 9. A machine screw 18 is further shown in FIG. 10.

Figure 11A:
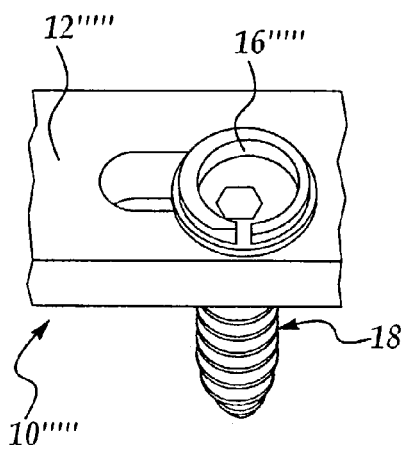
FIGS. 11A, 11B, and 11C are various perspective views of an embodiment of the bone plate assembly of the present invention wherein the apertures are slotted and a cylindrical screw travels along a longitudinal distance of the slotted aperture in the base plate.
Figure 11B:
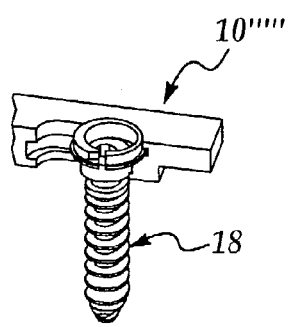
Figure 11C:
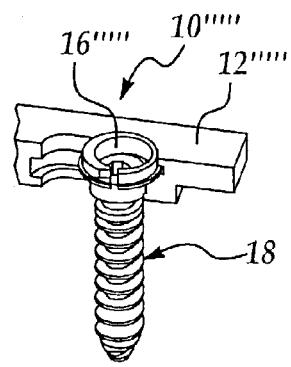

Another variation of the screw retaining mechanism 16"" and related slotted apertures 14 located on the bone plate assembly 10"" shown in FIGS. 11A, 11B, and 11C. In this particular embodiment, the cylindrical screw head 20 travels in the slot 14"" along the base plate 12"". The screw retaining mechanism 16"" prevents the screw 18 from backing out through the aperture 14"" therein.

Another embodiment of both the bone plate assembly 12"" and the screw retaining mechanism 16"" of the present invention is illustrated in FIGS. 16, 17, 18, 19, and 20. As with the other embodiments of the present invention disclosed herein, this embodiment is based on the concept of allowing a portion of the screw retaining mechanism 16 to cover a portion of the screw head 20 to prevent the screw 18 from backing out from the base plate 12. Instead of rotating the screw retaining mechanism 16"" to cover at least a portion of the screw head 20 however, the screw retaining mechanism 16"" is slid along a groove 50 machined along the side walls 51 of the aperture 14"" of the base plate 12"" therein.

The embodiment of the base plate assembly 12"" illustrated in FIGS. 16-20 utilizes at least one bone screw 18 for fixation of adjacent vertebrae of a spine that includes a base plate 12"" including at least one aperture 14 extending therethrough. Typically, the aperture 14"" is an elongated slot having a hole 49 extending therethrough and walls 51 forming a spherical seat 52 a distance along a length of the slot 52 to allow the screw 18 to enter through the hole 49. The walls 51 include at least one protrusion 56 extending into the hole 49 and at least one undercut 58 situated within the aperture 14"" of the base plate 12"". The bone plate assembly 10"" also includes a screw retaining mechanism 16"" mountable and slidably movable on the base plate 12"" between locked and unlocked positions relative to the aperture 14"" for preventing a bone screw 18 from backing out from the base plate 12"". The screw retaining mechanism 16"" includes a bottom portion 60, a top portion 62, and two side portions 64. The bottom portion 60 has a spherically-shaped recess 66. The top portion 62 has a first recess 63 forming a substantially U-shaped inner surface 63 and a second surface 65 extending arcually further radially outward relative to the first surface 63. The side portions 64 have lip mechanism 68 radially extending from the center of the screw retaining mechanism 16. The lip mechanism 68 is for engaging the undercut 58 situated within the aperture 14'''''' of the base plate 12''''''. The side portions 64 further include at least one indentation 70 that operatively engages the protrusions 56 within the aperture 14'''''' of the base plate 12''''''. There is a small round indentation 72 located within the aperture 14'''''' that is used to place or seat an instrument within the aperture 14'''''' to move the screw retaining mechanism 16'''''' between locked and unlocked positions.

The aperture 14'''''' allows for the longitudinal movement of the screw 18 along the distance of the slot while the screw retaining mechanism 16'''''' is in the locked position. The protrusions 56 operatively engage the indentations 70 of the screw retaining mechanism 16'''''' in a locked position. Further, as with other embodiments of the base plate 12'''''', the aperture 14'''''' allows for the screw 18 to translate without being able to rotate about the spherical head of the other variation.

In operation, the above described embodiment as illustrated in FIGS. 16 to 20 initially proceeds by placing the plate against the bone and the inserting the bone screws 18 inserted through the base plate 12'''''' into the bone and tightened securely. A small instrument is then introduced into the slot 54 behind the screw retaining mechanism 16'''''' and pushes the screw retaining mechanism 16'''''' over the top of the screw 18 until the indentations 70 engage the extended protrusions 56.

Figure 12:
FIG. 12 is an embodiment of the screw retaining mechanism wherein the screw retaining mechanism is substantially "U" shaped.
Figure 13:
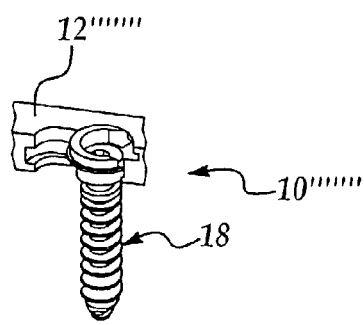
FIG. 13 is a perspective, cross-sectional view of an embodiment of the bone plate assembly wherein the screw retaining mechanism that is illustrated in detail in FIG. 12 is shown in combination with the bone screw, wherein the screw retaining mechanism is in a locked positioned.
Figure 14A:
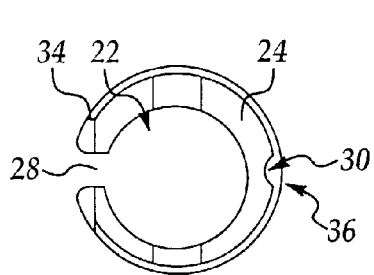
FIG. 14 is an engineering diagram illustrating an embodiment of the bone plate assembly and the screw retaining mechanism of the present invention.
Figure 14B:
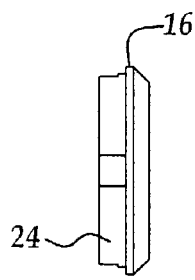
Figure 14C:
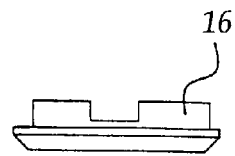
Figure 14D:
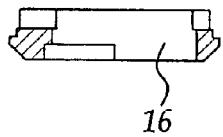
Figure 14E:
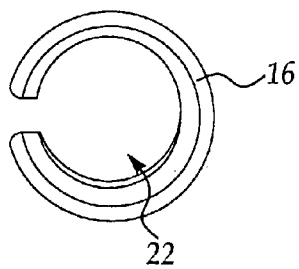
Figure 15A:
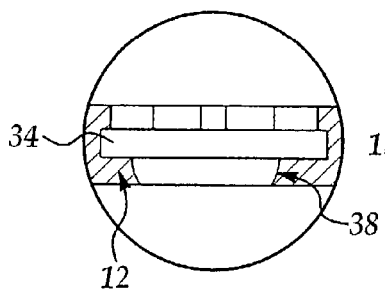
FIG. 15 is an engineering diagram illustrating an-embodiment of the bone plate assembly and the screw retaining mechanism of the present invention.
Figure 15B:
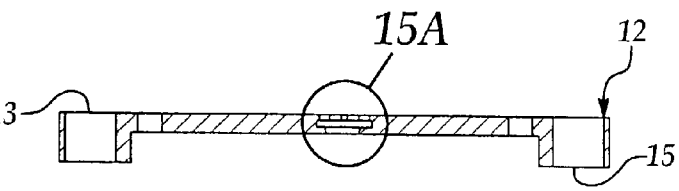
Figure 15C:
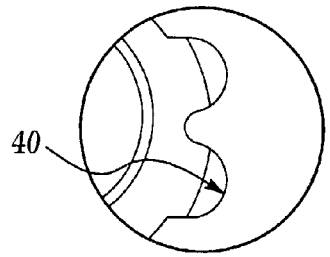
Figure 15D:
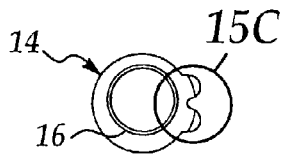

Further variations of the present invention include the screw retaining mechanism 16'''''' having a substantially U-shaped opening to prevent the screw 18 from backing out. The screw retaining mechanism 16'''''' can be moved for blocking at least a portion or covering at least a portion of the screw head 20 and/or screw opening to prevent the screw 18 from backing out from its position. Such a screw retaining mechanism 16'''''' is illustrated in FIGS. 12 and 13. In FIG. 13, the screw retaining mechanism 16'''''' is in its locked position.

As previously mentioned, a variation of the present invention includes an added insert 74 to be placed within any type of base plate 12. This insert 74 has the appropriate machined grooves, tabs, extensions, spherical seats, and other features required to accommodate all types of screw retaining mechanisms 16. Depending upon the type of screw retaining mechanism 16 utilized, the type, shape, design, and size of the machined insert 74 varies. The advantage of the machined insert 74 is that the insert 74 would be machined accordingly as opposed to machining the entire base plate 12. The base plate 12 merely needs to be punched-out, cut, or formed to provide a hole 76 in which to place the insert 74 therein. This results in increased compatibility with currently existing base plates 12 and also increases the various combinations of screw retaining mechanisms 16, machined inserts 74, and base plates 12 that can be formed. This variation is further illustrated in FIG. 21, wherein FIG. 21A shows the base plate 12 with a round hole 76, FIG. 21B shows the insert 74, and FIG. 21C shows the screw retaining mechanism 16.

Throughout this application, various publications are referenced by author and year. United States Patents on the other hand, are referenced by their numbers. Full citations for the publications are listed below. The disclosures of these publications and patents in their entireties are hereby incorporated by reference into this application in order to describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

What is claimed is:

1. A bone plate assembly comprising: a base plate defining at least one elongated slot and a hole, the hole having an outer perimeter inside an outer perimeter of the elongated slot offset from a center of the elongated slot outer perimeter and extending through the base plate; and a screw retaining mechanism mounted within the elongated slot and slidably movable between locked and unlocked positions relative to the hole along a side surface of the base plate defining the outer perimeter of the slot, said screw retaining mechanism including a top portion and opposed side portions with a recess between the side portions, the screw retaining mechanism configured such that in the locked position, the screw retaining mechanism encircles a portion of a screw received within the hole.

2. The assembly according to claim 1, wherein said screw retaining mechanism includes a tab for engaging at least one groove located along an outer edge of the elongated slot in a side surface of the base plate.

3. The assembly according to claim 1, wherein said screw retaining mechanism does not block a portion of a screw disposed through said hole thereby defining said unlocked position.

4. The assembly according to claim 1, wherein said screw retaining mechanism engages the screw in the locked position and prevents any movement thereof.

5. The assembly according to claim 1, wherein said screw retaining mechanism allows the screw to pivot freely while said screw retaining mechanism is in said locked position.

6. The assembly according to claim 1, wherein said screw retaining mechanism is removably mounted within the elongated slot of the base plate.

7. The assembly according to claim 1, wherein said screw retaining mechanism maintains the screw below an upper surface of the base plate when in said locked position.

8. The assembly according to claim 1, wherein said screw retaining mechanism is U-shaped.

9. The assembly according to claim 1, wherein said screw retaining mechanism is compressible about said central axis.

10. The assembly according to claim 1, wherein said screw retaining mechanism includes a bottom portion having a spherically-shaped recess.

11. The assembly according to claim 10, wherein the recess forms a substantially U-shaped inner first surface.

12. The assembly according to claim 11, wherein the recess further includes a second surface extending arcuately further radially outward relative to said first surface.

13. The assembly according to claim 1, wherein each of said side portions includes an indentation which operatively engages protrusions on the base plate in a locked position.

14. An insert for placement into an aperture of a base plate comprising screw retaining means mountable and slidably movable on a plate between locked and unlocked positions relative to an aperture for preventing a bone screw from backing out from the base plate, wherein said screw retaining means includes a bottom portion, a top portion, and two side portions, said bottom portion having a spherically-shaped recess, said top portion having a first recess forming a substantially U-shaped inner surface and a second surface extending arcually further radially outward relative to said first surface such that the second surface defines a larger opening into the first recess, and said side portions having lip means radially extending therefrom for engaging an undercut situated within the aperture of the base plate.

15. The insert according to claim 14, wherein said side portions further include an indentation that operatively engage over protrusions that extend into the aperture on the base plate.

* * * * *